(12) United States Patent
Raghuraman et al.

(10) Patent No.: US 7,432,109 B2
(45) Date of Patent: Oct. 7, 2008

(54) SPETROSCOPIC PH MEASUREMENT USING OPTIMIZED MIXTURES OF REAGENTS TO EXTEND MEASUREMENT RANGE

(75) Inventors: Bhavani Raghuraman, Wilton, CT (US); Gale H. Gustavson, Brookfield, CT (US); Emilie Dressaire, Beziers (FR); Oleg Zhdaneev, Tomsk (RU); Ronald Van Hal, Ridgefield, CT (US); Oliver Mullins, Ridgefield, CT (US); Philippe Salamitou, Mamaroneck, NY (US)

(73) Assignee: Schlumberger Technology Corporation, Ridgefield, CT (US)

( * ) Notice: Subject to any disclaimer, the term of this patent is extended or adjusted under 35 U.S.C. 154(b) by 881 days.

(21) Appl. No.: 10/782,209

(22) Filed: Feb. 19, 2004

(65) Prior Publication Data
US 2004/0219064 A1     Nov. 4, 2004

(30) Foreign Application Priority Data
Nov. 22, 2002 (GB) .................. 0227267.2

(51) Int. Cl.
*G01N 31/22* (2006.01)
*G01N 21/00* (2006.01)
(52) U.S. Cl. .................. 436/163; 436/164

(58) Field of Classification Search .............. None
See application file for complete search history.

(56) References Cited

FOREIGN PATENT DOCUMENTS

JP     60202359     12/1985

OTHER PUBLICATIONS

Baldini et al. "In vivo optical—fibre pH sensor for gastro-oesophageal measurements", Sensors and Actuators B. 1995, v. 29, pp. 164-168.*
Lin et al., "An Optical pH sensor with a linear response over a broad range." Analytica Chimica Acta 408 (2000) 49-55.
King et al., "Spectral Modeling of Sulfonephthalein Indicators: Application to pH measurements using Multiple Indicators", Applied Spectroscopy, vol. 44, No. 4, 1990, pp. 722-727.
Netto et al., "A fiber-optic broad-range pH sensor system for gastric measurements", Sensors and Actuators B 29 (1995) 157-163.
Bates, R. G. *Determination of pH: Theory and Practice*. John Wiley (1964) Chapter 6 pp. 131-171.

(Continued)

*Primary Examiner*—Yelena G Gakh
(74) *Attorney, Agent, or Firm*—James McAleenan, Esq.; Vincent Loccisano, Esq.; Jody Lynn DeStefanis, Esq.

(57) ABSTRACT

An indicator mixture that allows pH measurement over a broader range of pH or to a higher accuracy than available using conventional spectroscopic techniques. In particular, the mixture of the present invention is comprised of two or more reagents such that when combined, the reagent mixture is capable of either detecting: (1) a pH range broader or more accurate than that the reagents individually, or (2) pH more accurately than the reagents individually. Also disclosed are methods of making and using the mixture.

11 Claims, 11 Drawing Sheets

OTHER PUBLICATIONS

Bevington, P.R. and Robinson, D.K. *Data Reduction and Error Analysis for the Physical Sciences.* McGraw Hill, 3rd Edition, (2003) Chapter 3, pp. 36-41.

Vogel, A.I. *A Text-Book of Quantitative Inorganic Analysis.* John Wiley, 3rd Edition (1961) Chapter I,.30. p. 59.

Wright, John C. *Authentic Learning Environment in Analytical Chemistry Using Cooperative Methods and Open-Ended Laboratories in Large Lecture Courses.* Journal of Chemical Education.(Sep. 1996) vol. 73, p. 827.

* cited by examiner

SPECTROSCOPIC PH MEASUREMENT USING OPTIMIZED MIXTURES OF REAGENTS TO EXTEND MEASUREMENT RANGE

The present invention claims priority to co-pending U.S. patent application Ser. No. 10/667,639 filed Sep. 22, 2003, entitled "Determining Fluid Chemistry of Formation Fluid by Downhole Reagent Injection Spectral Analysis," which in turn claims priority to co-pending GB patent application no. 0227267.2 filed Nov. 22, 2002, entitled "Apparatus and Method for Analysing Downhole Water Chemistry." Both of these patent applications are incorporated by reference herein in their entireties.

FIELD OF THE INVENTION

The present invention relates to pH measurement of aqueous samples using pH sensitive reagents (such as dyes) and, more particularly, to a reagent mixture that allows accurate pH measurement over an extended measurement range.

BACKGROUND

Spectroscopic (or calorimetric) method for pH measurement is a well-established technique, wherein a pH sensitive reagent (or dye) changes color based on the pH of the solution. The theory of spectroscopic pH measurement using a single reagent indicator is well known (see Bates, "Determination of pH: Theory and Practice" Chapter 6 (1964), incorporated by reference herein in its entirety) and can be characterized by the following equation:

$$\text{pH} = pKa + \log\frac{\gamma_B}{\gamma_A} + \log\frac{B}{A} \quad (1)$$

where Ka is the thermodynamic acid dissociation constant for the reagent, which is a function of temperature and pressure; A, B are concentrations of the acid and base forms of the reagent, respectively; $\gamma_A$, $\gamma_B$ are activity coefficients of the acid and base forms of the reagent, respectively, which are a function of temperature, pressure and ionic strength of the solution.

The ratio of the base form to the acid form (B/A) of the reagent indicator may be calculated from spectral measurements using the following equations:

$$C_T = A + B \quad (2)$$

$$OD^{\lambda 1} = \epsilon_A^{\lambda 1} lA + \epsilon_B^{\lambda 1} lB \quad (3)$$

$$OD^{\lambda 2} = \epsilon_A^{\lambda 2} lA + \epsilon_B^{\lambda 2} lB \quad (4)$$

$$ODR_{\lambda 1}^{\lambda 2} = \frac{OD^{\lambda 2}}{OD^{\lambda 1}} \quad (5)$$

$$\frac{B}{A} = \frac{ODR_{\lambda 1}^{\lambda 2}\left(1 - \frac{\epsilon_A^{\lambda 2}}{\epsilon_A^{\lambda 1}}\frac{1}{ODR_{\lambda 1}^{\lambda 2}}\right)}{\frac{\epsilon_B^{\lambda 2}}{\epsilon_A^{\lambda 1}}\left(1 - \frac{\epsilon_B^{\lambda 1}}{\epsilon_B^{\lambda 2}}ODR_{\lambda 1}^{\lambda 2}\right)} \quad (6)$$

where $OD^{\lambda i}$ is the optical density measured at wavelength $\lambda_i$; l is path length; A, B are the respective concentrations of acid and base forms of the reagent in the sample-reagent mixture; $C_T$ is the total reagent concentration in the sample-reagent mixture; $\epsilon_A^{\lambda i}$, $\epsilon_B^{\lambda i}$ are molar extinction coefficients at wavelength $\lambda_i$ for A, B, respectively; and $ODR_{\lambda 1}^{\lambda 2}$ is the optical density ratio as defined in Equation (5).

The pH of a sample can be determined using spectral measurements by substituting Equation (6) in Equation (1). Because the acid and base form concentrations appear only as a ratio in Equation (1) and the absolute concentration of the reagent does not appear in Equations (1) or (5), the pH calculation is independent of the reagent concentration and the volume of the reagent added to the sample. If the ionic strength of the sample is at least an order of magnitude greater than the reagent concentration in the reagent-sample mixture, then the ionic strength of the sample and the activity coefficients (see Equations (7) and (8) below) are independent of reagent concentration. Accordingly, the only requirements for reagent addition are that the reagent concentration be (a) within a range where Beer's law is satisfied, (b) below an upper limit depending on the buffer strength of the sample beyond which the addition of the reagent could alter the sample pH, and (c) high enough to allow a good signal-to-noise ratio.

The molar extinction coefficients for the acid and base forms are obtained by calibration using solutions having pH values wherein the reagent exists completely in either its acid form or its base form. Alternatively, if the total reagent concentration is known very accurately, pH may be determined by measuring absorption at a single wavelength. However, because small errors in absolute concentration ($C_T$) can cause large errors in pH calculation, this method may not provide an accurate pH measurement. The pH of a sample may also be calculated using a continuous spectral scan in the relevant region and applying regression analysis to determine the base to acid ratio.

From Equation (1), as pH values move away from the pKa values of a given reagent, the acid or the base fraction of the reagent becomes very small. Due to the low signal-to-noise ratios, the error in the pH measurement increases as pH values move away from the pKa value. Thus, for example, for a pH value 2 units lower than the pKa value, the fraction of the base form of the reagent is only 1%. Consequently, the OD corresponding to the base form peak wavelength is very low, resulting in inadequate pH accuracy. With single reagent indicators, the typical range of pH measurement is limited to about 1 to 1.5 units on either side of the reagent's pKa value. Beyond this range, a different reagent with a more appropriate pKa value must be used. Accordingly, the spectroscopic technique is less flexible to implement because knowledge of the sample's pH range is required a priori so that the appropriate reagent indicator is selected.

A commonly used pH indicator uses a mixture of reagents to extend the range of pH measurement. Visual observation of color allows pH determination to within 1 unit (see Vogel, "Text-Book of Quantitative Inorganic Analysis" 3$^{rd}$ Edition, Chapter 1.30, page 59 (1961), incorporated by reference herein in its entirety). However, it is difficult to obtain highly accurate measurements using spectroscopic techniques because the visible spectrum of the mixed reagent is generally a cumulative addition of the spectra of individual reagents. Unless the individual spectra are well resolved, it is difficult to invert the fraction of each form for accurate pH calculation.

Additional factors must be considered when performing pH analysis downhole. For example, only a limited number of reagents (pH indicators) can be transported downhole, the nature of the sample cannot be determined a priori, and only limited spectral analysis can be performed downhole. Accordingly, it would be useful to have a broad pH indicator that allows for simple, yet accurate, pH determination. Further, it is difficult to control the amount of reagent added to the sample under investigation in the downhole environment. Accordingly, a pH measurement that is not dependent on reagent concentration would be preferred.

Accordingly, it is an object of the present invention to provide an indicator mixture that retains the advantages of the single reagent method and that is effective over a broad range of pH values.

It is a further object of the present invention to provide a spectroscopic technique to determine the pH of a sample with the accuracy levels comparable to single reagent spectroscopy over a broad range of pH values.

It is yet another object of the present invention to provide a reagent mixture suitable for use in a downhole environment.

SUMMARY OF THE INVENTION

The present invention relates to the use of a reagent mixture that allows pH measurement over a broader range of pH than available using conventional spectroscopic techniques. In one embodiment of the present invention, a fluids analyzer for determining the pH of formation fluid in a region of earth formation surrounding a borehole is disclosed comprised of: a reagent container having a mixture of two or more reagents wherein the reagent mixture is capable of detecting either: (1) a pH range broader than each reagent individually or (2) pH more accurately than each reagent individually; and means for mixing formation fluid with the reagent mixture downhole. The fluids analyzer may further include a spectral analyzer means, coupled to receive a mixture of formation fluid and the reagent-mixture from the mixing means for analyzing the optical density of the mixture of formation fluid and reagent mixture in two or more spectral channels. The reagent mixture is capable of measuring pH to an accuracy of about 0.5 units or better. Typical downhole spectral analyzers use spectral channels having bandwidths of approximately 10-20 nm.

A second embodiment of the present invention is a method of making a reagent mixture for determining the pH of a sample comprising: (a) identifying a target pH range; (b) mixing known relative quantities of two or more reagents to create a reagent mixture, wherein the reagent mixture is capable of detecting either: (i) a pH range broader than each reagent individually or (ii) pH to a better accuracy than the reagents individually; (c) optimizing the reagent mixture to identify one or more sets of reagents to be mixed that satisfy the targeted pH range; and (d) characterizing at least one set of reagents.

The sets of reagents may be optimized by identifying one or more sets of reagents by carefully selecting the thermodynamic acid dissociation constants of the reagents, adjusting the relative quantities of the reagents, or adjusting (the bandwidth and/or wavelength of) the spectral channels. This optimization process may be performed by trial and error, or experimentation. It is noted that in some cases optimization may be generally viewed as an error minimization technique; however, optimization may be performed to improve other parameters of interest, such as maximizing sensitivity of pH measurement or signal-to-noise ratio. Alternatively, forward models and algorithms may be developed based on thermodynamic acid dissociation constants, relative quantities (or fractions), and the spectral channels. Once "optimal" reagent sets are identified, at least one of the sets should be characterized to determine the detectable pH range of the mixture. Further, an error analysis should be performed to determine the accuracy of the mixture to measure pH. It is further noted that the absolute concentration of the reagent mixture may be optimized to improve signal-to-noise ratio and reduce the effects of error.

In a third embodiment, a method for determining the pH of formation fluid in a region of earth formation surrounding a borehole is disclosed comprising: (a) storing a reagent mixture in a reagent container coupled to a fluids analyzer, wherein the reagent mixture is capable of detecting either: (i) a pH range broader than each reagent individually or (ii) pH to a better accuracy than each reagent individually; (b) positioning the fluids analyzer downhole; (c) drawing formation fluid into the fluids analyzer; (d) mixing formation fluid and the reagent mixture; and (e) analyzing the optical density of said mixture of formation fluid and reagent mixture in one or more channels to determine the pH of the formation fluid. If only one spectral channel is used, the absolute concentration of the reagent mixture should also be determined. However, if two spectral channels are used, then it is not necessary to determine the absolute concentration of the reagent mixture.

Accordingly, the present invention provides a pH indicator mixture for spectroscopic techniques that is accurate over a broader pH range (as compared to conventional spectroscopic methods). As will be described in detail below, the method disclosed herein uses either (1) two or more spectral channels or (2) one spectral channel and accurate (absolute) reagent concentrations. If optical density (OD) measurements (or transmission, absorption or other spectral measurements which may be converted to OD) at two spectral channels are used, reagent concentration in the sample-reagent mixture is not needed; instead the relative quantities (fractions) of the reagent in the mixture may be used. Furthermore, the reagents need not have well resolved individual spectra. In fact, the accuracy of the method is enhanced if the spectra of the acid and base forms of one reagent are substantially similar to the spectra of the acid and base forms of the other, respectively. Because there is a vast pool of reagents to choose from, it is relatively simple to pick reagents that show similar direction of color change with pH though at different pKa values. Accordingly, the present invention includes algorithms to optimize for the choice of reagents (i.e., their pKa values) based on the pH measurement range of interest. Further, the individual reagent fractions in the mixture may be selected to obtain an optimized mixture over the pH range of interest. It is noted that while the discussion that follows relates to the use of two reagents, the method may be easily extended to three or more reagents.

For the purposes of the present invention, the term "optical techniques" is intended to apply to a broad range of techniques, including but not limited to, spectroscopic, calorimetric, optical, etc. It is further noted that for the purposes of the present invention, the terms "pH sensitive reagent," "reagent," and "dye indicator" are used interchangeably.

Further advantages and novel features of the invention will be set forth in the description which follows.

DETAILED DESCRIPTION

Figure 1:
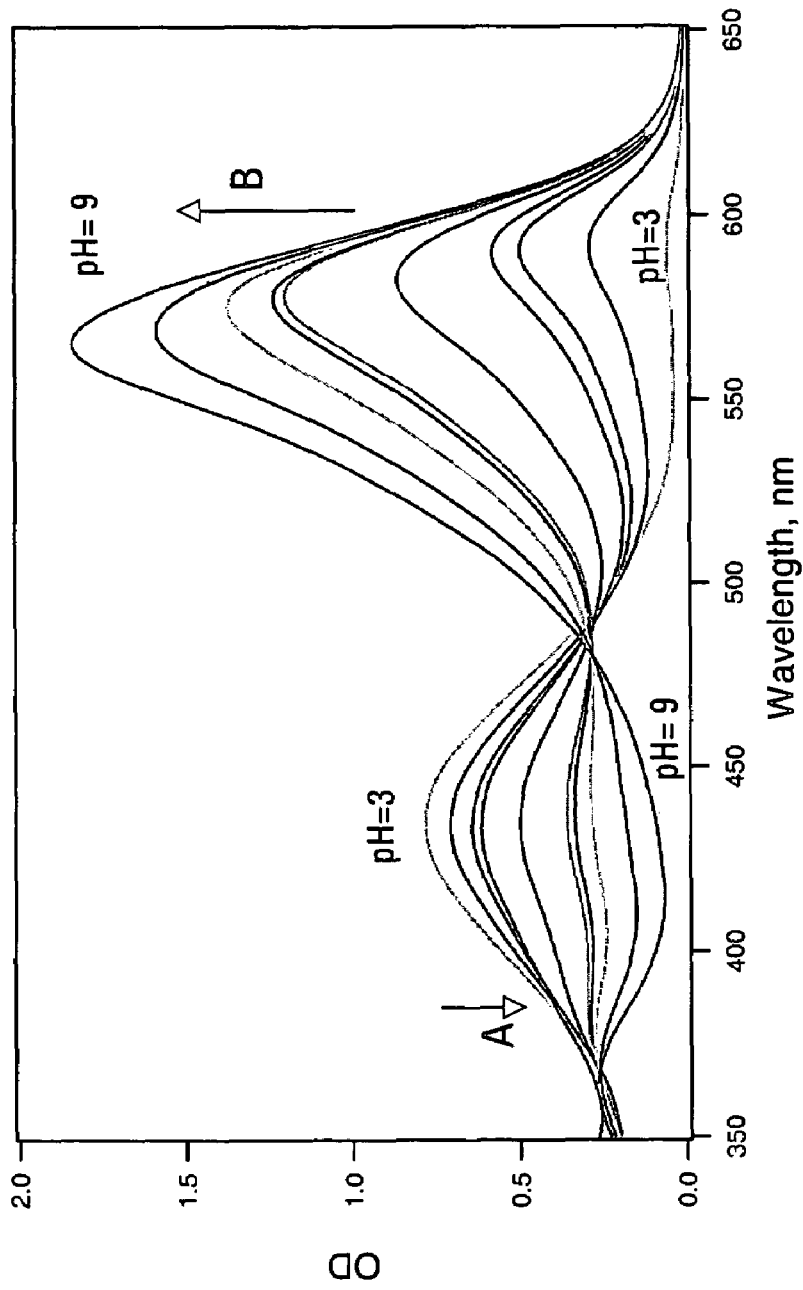
FIG. 1 is a plot showing the spectra of a three-reagent mixture in buffer solution with pH varying from 3 to 9.

The present invention relates to a spectroscopic technique accurate over a broader pH range (as compared to conventional spectroscopic methods) using reagent mixtures. As will be described in detail below, the method disclosed herein uses either (1) two or more spectral channels or (2) one spectral channel and accurate reagent concentrations. If two spectral channels are analyzed, reagent concentration in the sample-reagent mixture is not needed; instead the relative quantities (fractions) of the reagent in the mixture may be used. Furthermore, the reagents need not have well resolved individual spectra. In fact, the accuracy of the method is enhanced if the spectra of the acid and base forms of one reagent are substantially similar to the spectra of the acid and base forms of the other, respectively. Because there is a vast pool of reagents to choose from, it is relatively simple to pick reagents that show similar direction of color change with pH though at different pKa. Accordingly, the present invention includes algorithms to optimize for the choice of reagents (i.e., their pKa values) based on the pH measurement range of interest. Further, the individual reagent fractions in the mixture may be selected to obtain an optimized mixture over the pH range of interest. It is noted that while the discussion that follows relates to the use of two reagents, the method may be easily extended to three or more reagents.

Equations (1) through (6) may be rewritten for two reagents as follows:

$$pH = pKa_1 + \log\frac{\gamma_{B1}}{\gamma_{A1}} + \log\frac{B_1}{A_1} \tag{7}$$

$$pH = pKa_2 + \log\frac{\gamma_{B2}}{\gamma_{A2}} + \log\frac{B_2}{A_2} \tag{8}$$

$$C_{T1} = A_1 + B_1 \tag{9}$$

$$C_{T2} = A_2 + B_2 \tag{10}$$

$$f_1 = \frac{C_{T1}}{C_{T1} + C_{T2}} \tag{11}$$

$$OD^{\lambda 1} = \epsilon_{A1}{}^{\lambda 1} l A_1 + \epsilon_{B1}{}^{\lambda 1} l B_1 + \epsilon_{A2}{}^{\lambda 1} l A_2 + \epsilon_{B2}{}^{\lambda 1} l B_2 \tag{12}$$

$$OD^{\lambda 2} = \epsilon_{A1}{}^{\lambda 2} l A_1 + \epsilon_{B1}{}^{\lambda 2} l B_1 + \epsilon_{A2}{}^{\lambda 2} l A_2 + \epsilon_{B2}{}^{\lambda 2} l B_2 \tag{13}$$

$$ODR^{\lambda 2}_{\lambda 1} = \frac{OD^{\lambda 2}}{OD^{\lambda 1}} \tag{14}$$

where $A_1$, $B_1$ are acid and base form concentrations, respectively, of reagent 1 in the sample-reagent mixture; $A_2$, $B_2$ are acid and base form concentrations, respectively, of reagent 2 in the sample-reagent mixture; $C_{T1}$, $C_{T2}$ are total concentrations of reagent 1 and reagent 2, respectively, in the sample-reagent mixture; $f_1$ is the mole fraction of reagent 1 in the reagent mixture; $pKa_1$, $pKa_2$ are dissociation constants for reagents 1 and 2, respectively.

From Equations (7) through (14):

$$ODR^{\lambda 2}_{\lambda 1} = \frac{\sum_i \frac{B_i}{B_1} \frac{\varepsilon^{\lambda 2}_{Bi}}{\varepsilon^{\lambda 2}_{B1}}\left(1 + \frac{\varepsilon^{\lambda 2}_{Ai}}{\varepsilon^{\lambda 2}_{Bi}} 10^{-(pH-pKa_i)}\right)}{\sum_i \frac{B_i}{B_1} \frac{\varepsilon^{\lambda 1}_{Ai}}{\varepsilon^{\lambda 2}_{Bi}} \frac{\varepsilon^{\lambda 2}_{Bi}}{\varepsilon^{\lambda 2}_{B1}}\left(10^{-(pH-pKa_i)} + \frac{\varepsilon^{\lambda 1}_{Bi}}{\varepsilon^{\lambda 1}_{Ai}}\right)} \text{ for } i = 1, 2 \tag{15}$$

where $$\frac{B_2}{B_1} = \frac{1 + 10^{-(pH-pKa_1)}}{1 + 10^{-(pH-pKa_2)}} \frac{(1 - f_1)}{f_1} \tag{16}$$

Hence:

$$ODR_{\lambda 1}{}^{\lambda 2} = f(pH, \epsilon, pKa_1, pKa_2, f_1) \tag{17}$$

where $$\epsilon = (\epsilon_{A1}{}^{\lambda 1}, \epsilon_{B1}{}^{\lambda 1}, \epsilon_{A1}{}^{\lambda 2}, \epsilon_{B1}{}^{\lambda 2}, \epsilon_{A2}{}^{\lambda 1}, \epsilon_{B2}{}^{\lambda 1}, \epsilon_{A2}{}^{\lambda 2}, \epsilon_{B2}{}^{\lambda 2}) \tag{18}$$

From Equation (17), which is an analytical equation, once the reagents for the two-reagent mixture are chosen, the relative quantities, and wavelengths (width of the spectral channel) are selected, the ODR becomes a function only of the pH. It is independent of absolute reagent concentrations or volume of reagent mixture added to sample, and therefore retains the advantage of the single reagent measurement. The mixture may be characterized in terms of ODR and pH such that plots and look-up tables may be generated. Alternatively, Equation (17) may be inverted to express pH as an analytical function of ODR (such as by using a program like Mathematica by Wolfram Research, Inc.):

$$pH = f(ODR_{\lambda 1}{}^{\lambda 2}, \epsilon, pKa_1, pKa_2, f_1) \tag{19}$$

Equations (7) through (19) can be extended to a system of n reagents:

$$ODR_{\lambda 1}^{\lambda 2} = \frac{\sum_i \frac{B_i}{B_1} \frac{\varepsilon_{Bi}^{\lambda 2}}{\varepsilon_{B1}^{\lambda 2}} \left(1 + \frac{\varepsilon_{Ai}^{\lambda 2}}{\varepsilon_{Bi}^{\lambda 2}} 10^{-(pH-pKa_i)}\right)}{\sum_i \frac{B_i}{B_1} \frac{\varepsilon_{Ai}^{\lambda 1}}{\varepsilon_{Bi}^{\lambda 2}} \frac{\varepsilon_{Bi}^{\lambda 2}}{\varepsilon_{B1}^{\lambda 2}} \left(10^{-(pH-pKa_i)} + \frac{\varepsilon_{Bi}^{\lambda 1}}{\varepsilon_{Ai}^{\lambda 1}}\right)} \quad \text{for } i = 1, n \quad (20)$$

$$\frac{B_i}{B_1} = \frac{1 + 10^{-(pH-pKa_1)}}{1 + 10^{-(pH-pKa_i)}} \frac{f_i}{f_1} \quad \text{for } i = 1, n \quad (21)$$

$$ODR_{\lambda 1}^{\lambda 2} = f(pH, \epsilon, pKa_1, pKa_2 \ldots pKa_n, f_1, f_2 \ldots f_n) \quad (22)$$

where:

$$\epsilon = (\epsilon_{A1}^{\lambda 1}, \epsilon_{B1}^{\lambda 1}, \epsilon_{A1}^{\lambda 2}, \epsilon_{B1}^{\lambda 2}, \epsilon_{A2}^{\lambda 1}, \epsilon_{B2}^{\lambda 1}, \epsilon_{A2}^{\lambda 2}, \epsilon_{B2}^{\lambda 2} \ldots \epsilon_{An}^{\lambda 1}, \epsilon_{Bn}^{\lambda 1}, \epsilon_{An}^{\lambda 2}, \epsilon_{Bn}^{\lambda 2}) \quad (23)$$

Hence:

$$pH = f'(ODR_{\lambda 1}^{\lambda 1}, \epsilon, pKa_1, pKa_2 \ldots pKa_n, f_1, f_2 \ldots f_n) \quad (24)$$

It is noted that Equations (22) and (24) are analytical expressions.

FIG. 1 shows experimentally measured spectra for a three-reagent mix in pH buffers 3-9. Arrow A indicates decrease in OD of acid forms of reagents as buffer pH increases from 3 to 9. Arrow B indicates increase in OD of base forms of the reagents as buffer pH increases from 3 to 9. Reagent properties of these mixtures are summarized in Table 1.

Figure 2:
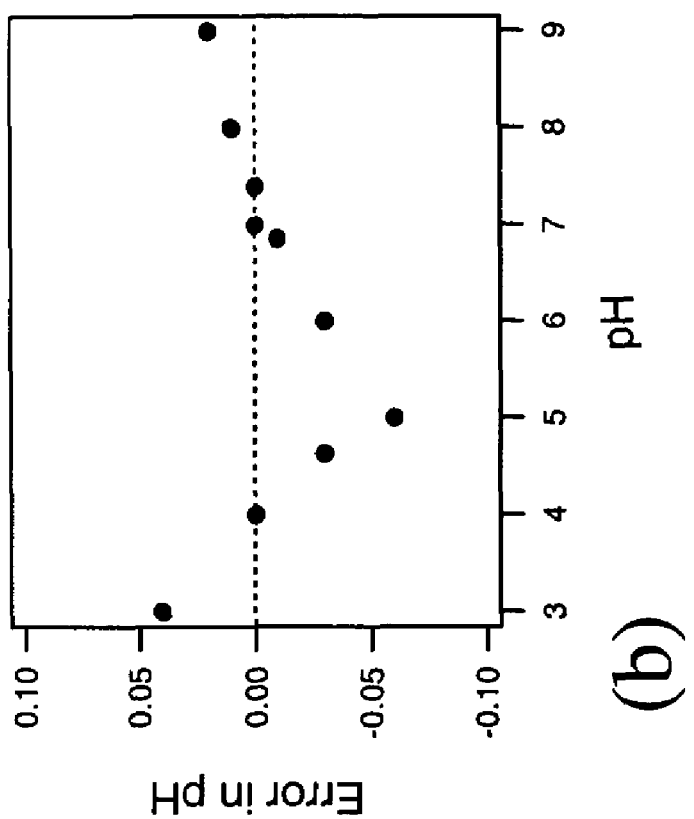
FIGS. 2(a) and (b) are plots: (a) comparing model predicted pH from experimental ODR values of FIG. 1 with true buffer pH values (445 and 570 nm wavelengths) and (b) showing the error in pH measurements as a function of pH.
Figure 2:
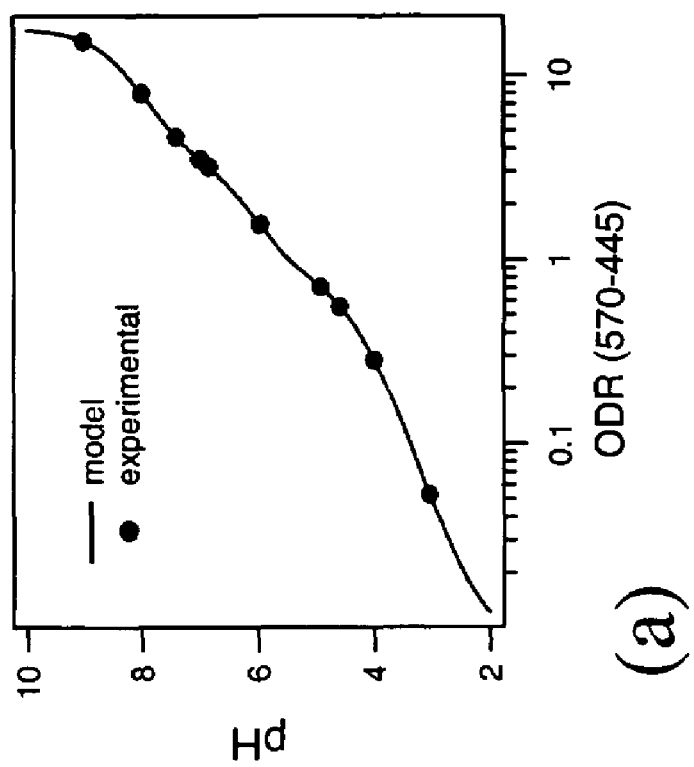

FIG. 2($a$) compares model predicted pH values calculated using measured ODR values of FIG. 1 with true pH values of the buffer solutions. FIG. 2($b$) plots the experimental error at various pH values. The reagent mixture of the example of FIG. 2($b$) is accurate over the range of buffers used (pH 3-9) with the errors within 0.06 pH units. Accordingly, the reagent mixture of the present invention is accurate over a broader pH range than the traditional single reagent indicators, which typically work over 2-3 pH units (see, for example, Table 2 below).

Figure 3:
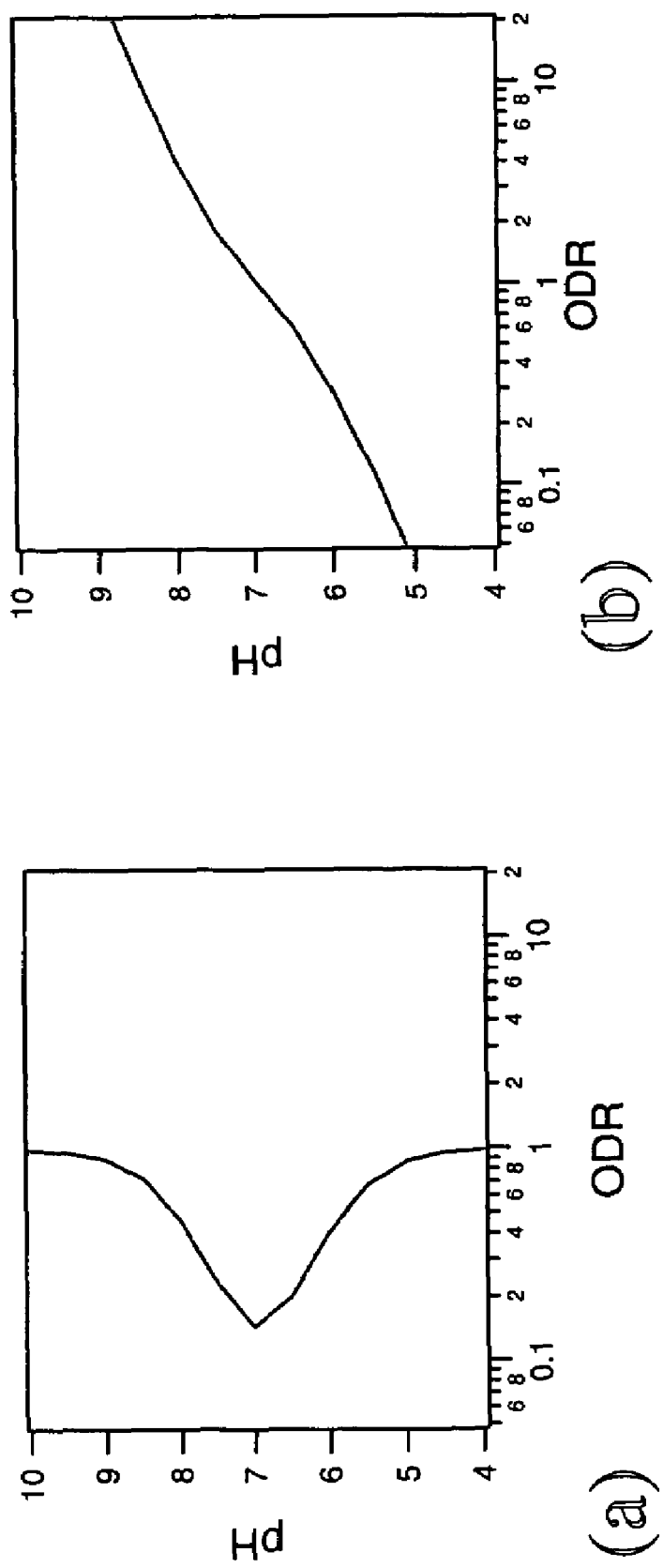
FIGS. 3(a) and (b) are plots: (a) showing a scenario where the acid form spectra of one reagent is identical to the base form spectra of the other and vice versa resulting in the pH being a non-unique function of ODR and (b) showing that pH is a unique function of ODR even when the acid and base forms of the two reagents have identical spectra.

FIG. 3($b$) shows the pH vs. ODR plot for two reagents (pKa$_1$=7.79, pKa$_2$=6.11, $f_1$=0.5) with identical spectra for its acid and base forms ($\epsilon_{A1}^{\lambda j} = \epsilon_{A2}^{\lambda j}$; $\epsilon_{B1}^{\lambda j} = \epsilon_{B}^{\lambda j}$ for all j). Here, the present invention works well. These results are contrary to conventional thinking where good spectral resolution would be preferred to calculate pH by inverting the spectra of the mixture for acid and base fractions of each reagent.

Like the single reagent measurement, the mixture of the present invention is independent of total amount of reagent added to the sample. Accordingly, the present methodology is easy to implement in batch or flow injection mode for measuring pH of aqueous samples. The method uses (1) a minimum of two spectral channels if concentration independence is desired or (2) one spectral channel and accurate reagent concentrations. The latter is very sensitive to absolute reagent concentrations and, hence, is potentially less robust. Alternatively, pH may be calculated using regression analysis, if spectral absorption (OD) data at more than two wavelengths or continuous scans are available.

Error Propagation and Analysis in pH Measurement

As mentioned above, a single reagent is sensitive only over a limited pH range around its pKa value. The extent of this range is determined by the accuracy required in the pH measurement and the spectroscopic noise. An error analysis should be performed to determine the measurable range as a function of these two parameters for single reagents and mixed reagents. An error analysis can also be performed to optimize for one or more of: the choice of reagents, relative quantities of the reagents, or spectral channels.

The method of error propagation is used to determine the standard deviation in pH measurement as a function of spectroscopic noise (standard deviation in OD) (Bevington et al., "Data Reduction and Error Analysis for the Physical Sciences," 3$^{rd}$ Edition, Chapter 3, pages 36-41, (2003), incorporated by reference herein in its entirety).

For $x = f(u, v)$, the standard deviation in x ($\sigma_x$) as a function of standard deviations in u ($\sigma_u$) and v ($\sigma_v$) is given as:

TABLE 1

Summary of reagent properties used in simulations

| | Phenol Red (reagent 1) | | Chlorophenol Red (reagent 2) | | Bromophenol Blue (reagent 3) | |
|---|---|---|---|---|---|---|
| | Acid | Base* | Acid | Base* | Acid | Base* |
| $\epsilon$ at 570 nm ($\lambda_2$) | 108 | 37975 | 58 | 54247 | 378 | 46859 |
| $\epsilon$ at 445 nm ($\lambda_1$) | 17916 | 3352 | 18136 | 1985 | 21711 | 1981 |
| Mol. wt. | 354.38 | 376.36 | 423.28 | 445.26 | 669.98 | 691.97 |
| pKa | 7.79 | | 6.11 | | 4.11 | |

*The base form is a sodium salt of the reagent.

The pH as calculated from Equation (24), however, is not necessarily always a unique function of ODR. FIG. 3($a$) is a plot showing two reagents (pKa$_1$=7.79, pKa$_2$=6.11, $f_1$=0.5) that are exact mirror images of each other; in this example, the spectrum of the acid form of one reagent is identical to the spectrum of the base form of the second reagent and vice versa ($\epsilon_{A1}^{\lambda j} = \epsilon_{B2}^{\lambda j}$; $\epsilon_{A2}^{\lambda j} = \epsilon_{B1}^{\lambda j}$ for all j). For each pH value there is a unique ODR. However, the inverse is not true; for a given ODR, there are two pH values and the method fails. By choosing reagents that show common direction of color change with pH (but at different pKa values), the sensitivity of the pH to ODR may be increased to obtain a unique solution.

$$\sigma_x \cong \sqrt{\sigma_u^2 \left(\frac{\partial x}{\partial u}\right)^2 + \sigma_v^2 \left(\frac{\partial x}{\partial v}\right)^2} \quad (25)$$

For a given reagent mixture (fixed pKa$_i$, $\epsilon$, $f_i$) and for a given set of wavelengths ($\lambda_1$, $\lambda_2$), the error propagation algorithm may be applied to Equations (20) and (24):

$$\sigma_{ODR_{\lambda1}^{\lambda2}} = ODR_{\lambda1}^{\lambda2} \cdot \sqrt{\left(\frac{\sigma_{OD^{\lambda2}}}{OD^{\lambda2}}\right)^2 + \left(\frac{\sigma_{OD^{\lambda1}}}{OD^{\lambda1}}\right)^2} \qquad (26)$$

$$\sigma_{pH} = \frac{\partial pH}{\partial ODR_{\lambda1}^{\lambda2}} \cdot \sigma_{ODR_{\lambda1}^{\lambda2}} \qquad (27)$$

Combining Equations (26) and (27), standard deviation in pH ($\sigma_{pH}$) measurement is obtained as a function of spectroscopic noise at the two wavelengths $\lambda_1$ and $\lambda_2$:

$$\sigma_{pH} = \frac{\partial pH}{\partial ODR_{\lambda1}^{\lambda2}} \cdot ODR_{\lambda1}^{\lambda2} \cdot \sqrt{\left(\frac{\sigma_{OD^{\lambda2}}}{OD^{\lambda2}}\right)^2 + \left(\frac{\sigma_{OD^{\lambda1}}}{OD^{\lambda1}}\right)^2} \qquad (28)$$

The derivative of pH with respect to ODR may be determined using the analytical expression of Equation (24) (which may be determined by inverting Equation (22) (such as by using packages such as Mathematica by Wolfram Research, Inc.).

Alternatively, because the expression is very long, the derivative from Equation (22) may be numerically calculated provided ODR is a continuous function of pH and differentiable at every point in the interval of interest.

$$\frac{\partial pH}{\partial ODR_{\lambda1}^{\lambda2}} = \frac{1}{\frac{\partial ODR_{\lambda1}^{\lambda2}}{\partial pH}} \qquad (29)$$

Figure 4:
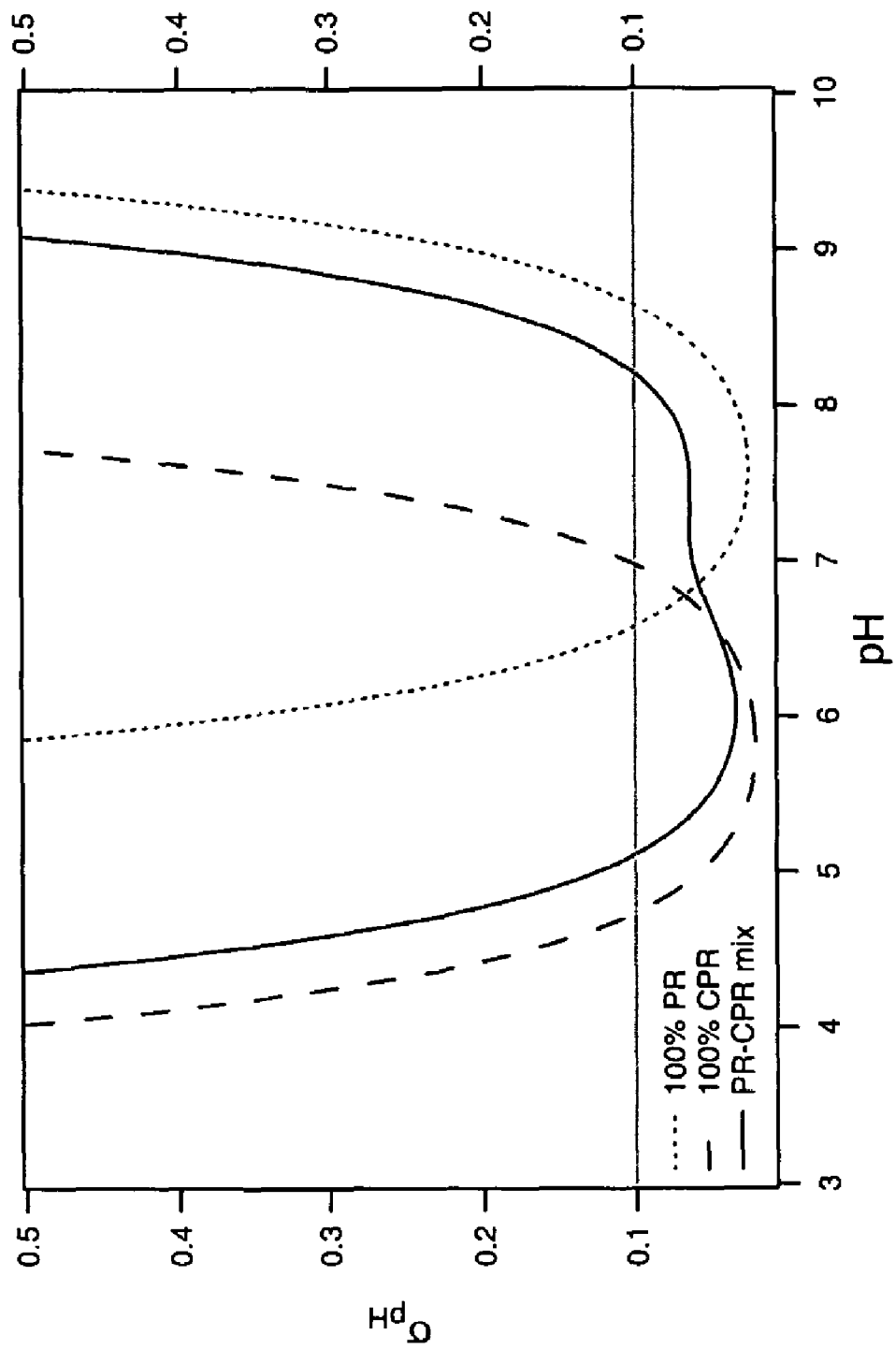
FIG. 4 is a plot showing the error estimation for single and two-reagent mixtures, allowing estimation of target pH intervals for any desired accuracy level (see Table 2 below).

FIG. 4 compares the standard deviation in pH as a function of standard deviation in OD (where spectroscopic noise is assumed to be 0.01 OD units and $C_T$ is $2 \times 10^{-5}$ M) for single reagents and for equal weight fraction mixture of the two reagents, PR and CPR from Table 1. This figure allows the measurable pH range to be estimated for a desired accuracy as a function of spectroscopic noise. Accordingly, the two-reagent mixture of this example allows measurement over a range longer than the single reagents mixtures (see also Table 2). It is noted that the addition of a third reagent will allow further extension of the measurement range.

TABLE 2

Extending range of pH measurements with reagent mixtures for 0.1 pH unit desired accuracy assuming spectroscopic noise of 0.01 OD units

| Reagent | Mole Fraction ($f_1$, $f_2$, $f_3$) | $C_T$, [M] | pH range |
| --- | --- | --- | --- |
| PR | 1.0, 0.0, 0.0 | $2 \times 10^{-5}$ | 6.6-8.7 |
| CPR | 0.0, 1.0, 0.0 | $2 \times 10^{-5}$ | 4.7-7.0 |
| BB | 0.0, 0.0, 1.0 | $2 \times 10^{-5}$ | 2.8-5.1 |
| PR-CPR | 0.55, 0.45, 0.0 (equal weight fractions) | $2 \times 10^{-5}$ | 5.1-8.2 |
| PR-CPR | 0.55, 0.45, 0.0 (equal weight fractions) | $4 \times 10^{-5}$ | 4.8-8.6 |
| PR-CRP-BB | 0.42, 0.35, 0.23 (equal weight fractions) | $2 \times 10^{-5}$ | 3.6-7.9 |
| PR-CRP-BB | 0.46, 0.26, 0.28 (optimized for pH 3.5 to 8) | $2 \times 10^{-5}$ | 3.5-8.1 |
| PR-CRP-BB | 0.42, 0.35, 0.23 (equal weight fractions) | $4 \times 10^{-5}$ | 3.2-8.5 |

From Equation (28), assuming equal noise at two wavelengths ($\sigma_{OD^{\lambda1}} = \sigma_{OD^{\lambda2}} = \sigma_{OD}$), $\sigma_{pH}$ increases linearly with $\sigma_{OD}$. Note also that while the pH calculation is independent of absolute reagent concentrations, the error in the pH measurement depends on absolute reagent concentration through the absolute OD values that appear in Equation (28). For a given reagent mixture with a fixed relative quantity of the individual reagents, the error in pH, $\sigma_{pH}$, decreases linearly with increasing absolute reagent concentration. However, as explained above, if concentration of the reagents added is very high, then concentration could affect the pH of the sample and introduce additional errors. Furthermore, the concentration may go beyond the range where Beer's Law is valid.

Optimization of Reagent Mixtures

Using the error estimation algorithm described above, the reagent mole fraction in the mixture may be optimized to minimize the error over a desired pH range. A possible formulation for the objective function for desired accuracy of 0.1 pH units, for example, over the interval $pH_1$ to $pH_2$, could include:

$$\text{Minimize } F(f_1, f_2, \ldots f_n) = \sum_{i=1}^{m} w_i(\sigma_{pH_i} - 0.1)^p \text{ for all } \sigma_{pH_i} \geq 0.1 \qquad (30)$$

where m is the number of discrete points into which the interval between $pH_1$ and $pH_2$ is divided and $w_i$ is the weight applied to the error contribution at each point. Both $w_i$ and p may be chosen to adjust the contribution of the error at each pH value in the desired range. This method provides the flexibility of having different levels of accuracy within a broader constraint of 0.1 pH units error. For example, by assigning a higher weight to the points in the interval between 5 and 6, one can optimize for 0.1 unit accuracy over the entire range of 4 to 9 with a higher level of accuracy between 5 and 6.

Figure 5:
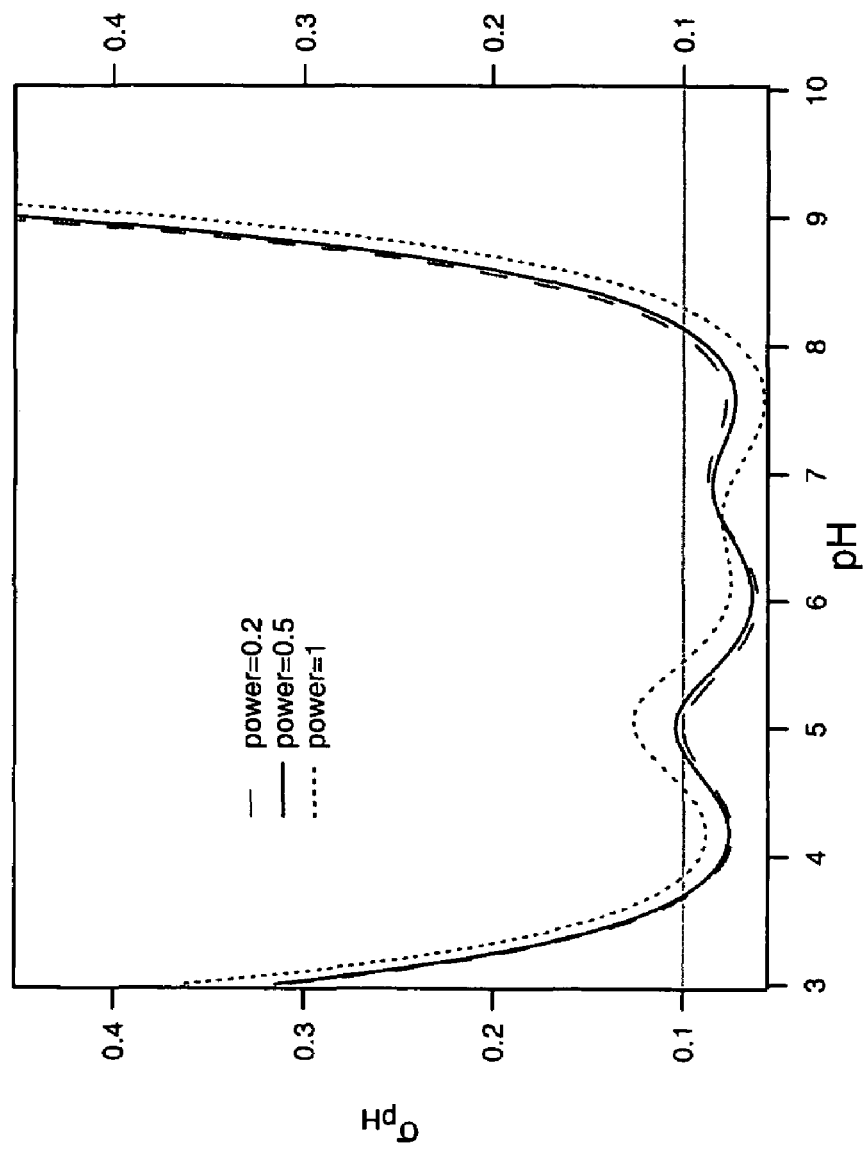
FIG. 5 is a plot showing the effect of changing the power p in the objective function [see Equation (30) below].

FIG. 5 shows the effect of varying power p with $w_i$ equal to one when optimizing over a pH range of 4-9 for a three-reagent mixture (reagent properties are summarized in Table 1). At pH equal to 9, the deviation from 0.1 units is very high. By using a power of 1, the contribution of error at 9 to the objective function Equation (30) is 0.27 units and is about 9 times higher than the contribution of the error at pH 5 (0.03 units). However, if the power p is 0.2, the contribution to the objective function of the error at pH 9 (0.77 units) is only 1.54 times higher as compared to the objective function error at pH 5 (0.5 units). In the second case with power p equal to 0.2, the optimization algorithm gives nearly equal importance to minimizing the error at pH 5 and pH 9, while in the first case the pH 9 error term dominates and the optimization algorithm ignores the error at pH 5. This is evident in the plots for the two cases.

While this is one form of the optimization function, one skilled in the art would recognize that other algorithms may be used to optimize reagent mixtures.

Standard minimization routines (such as the non-gradient simplex or amoeba DUMPOL algorithm in IMSL package from Visual Numerics, Inc.) can be used for the optimization of reagent mole fractions in the mixture.

Figure 6:
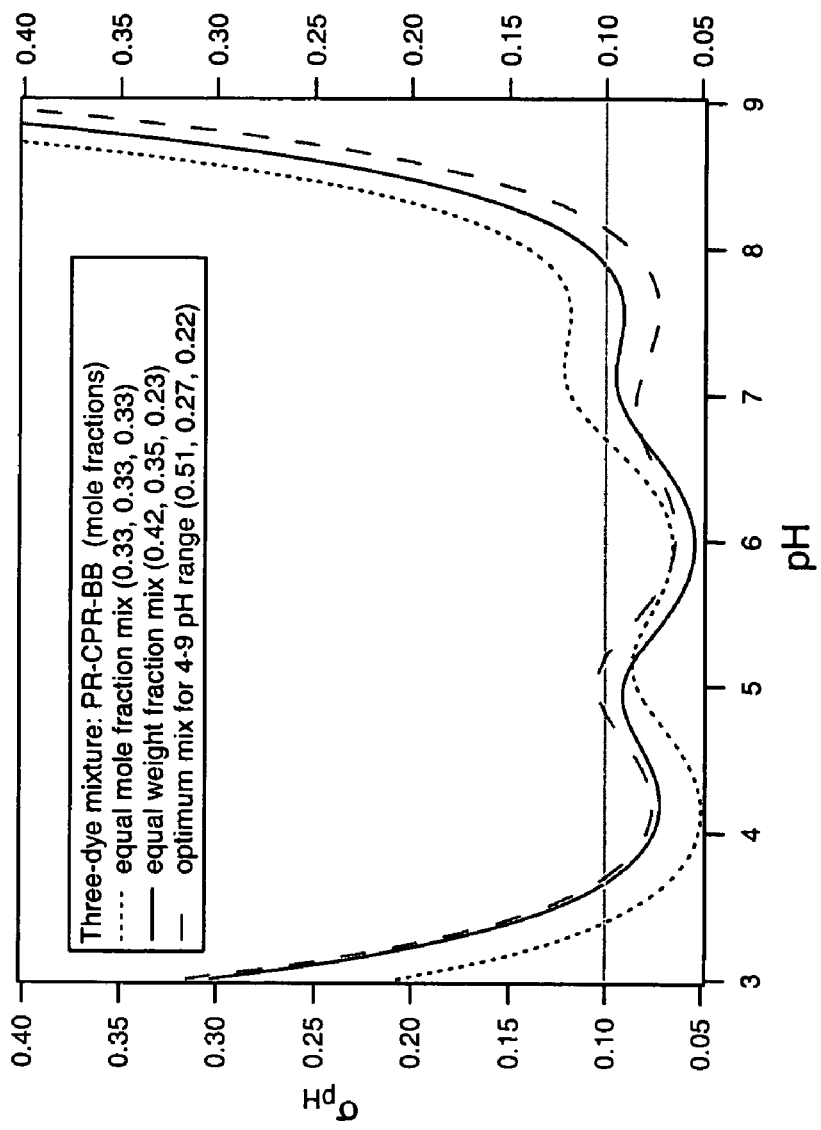
FIG. 6 is a plot showing that the optimization of the mole fractions in the three-reagent mixture yields better accuracy over the pH interval 4-9 as compared to using equal mole or weight quantities.

FIG. 6 shows the results of a three-reagent mixture optimized for pH range of 4 to 9 and compares with cases when equal weight and equal mole fractions are used. [Spectroscopic noise is assumed to be 0.01 OD units and total reagent concentration is $2 \times 10^{-5}$ M. For Equation (30), p is 0.5 and $w_i$ is 1.]

Figure 7:
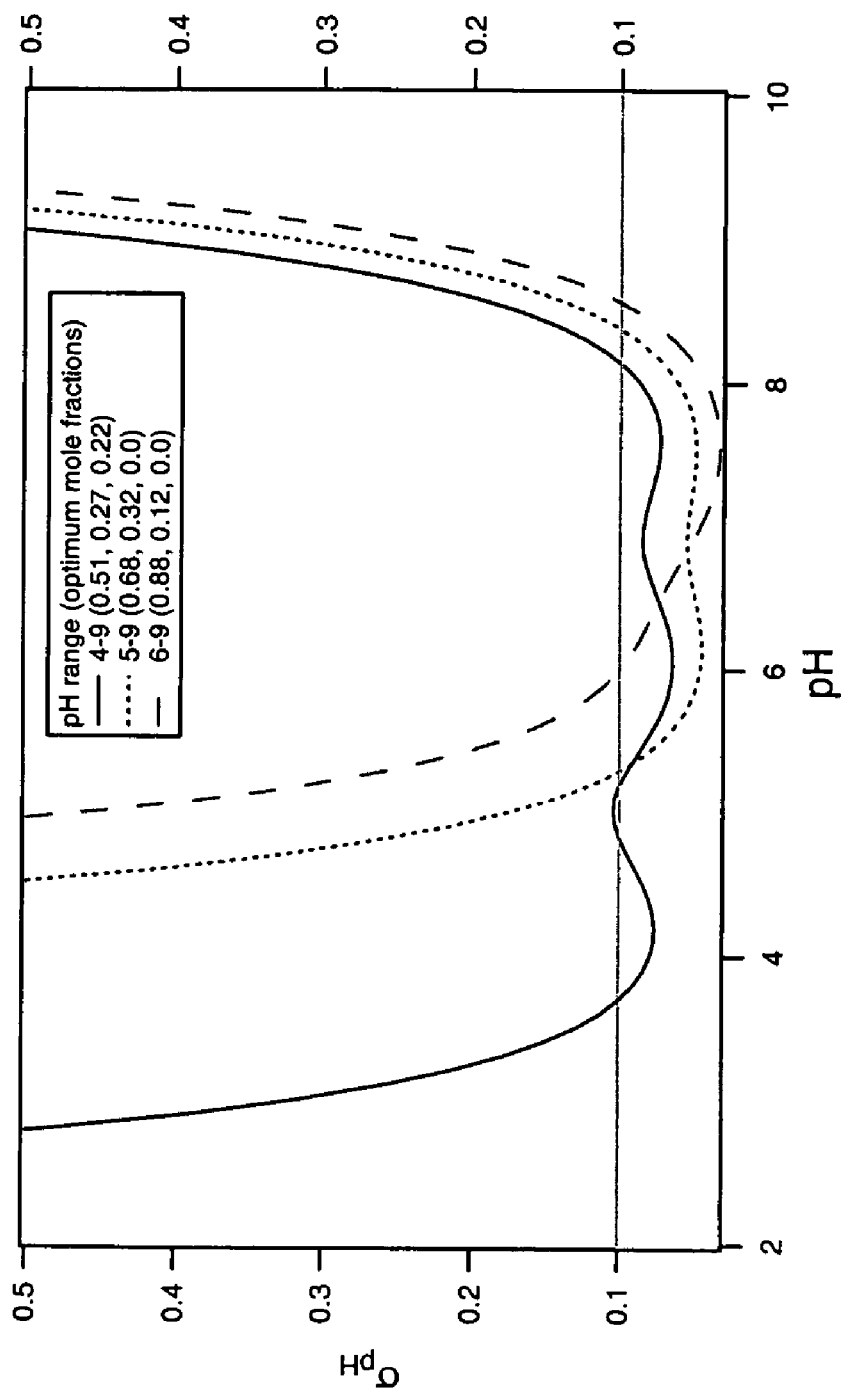
FIG. 7 is a plot showing the change in optimum reagent quantities with change in the target pH interval.

FIG. 7 shows how the optimization algorithm (see Equation (30)) adjusts mole fractions of the reagents in the mixture as the pH range of interest changes. As the pH range (pH 4-9) is shifted to a smaller interval of pH 6-9, the fraction of the reagent 1 (pKa=7.79) increases, while that of reagent 3 (pKa=4.11) falls to zero. [Spectroscopic noise is again assumed to be 0.01 OD units and total reagent concentration is $2\times10^{-5}$ M. For Equation (30), p is 0.5 and $w_i$ is 1.]

As discussed above, it is possible to obtain reagent combinations where the pH is a non-unique function of ODR. To prevent this, it is recommended that when a set of reagents are chosen, the mixture is forward modeled with known relative quantities or mole fractions of reagents to calculate pH as a function of ODR. The plot can be visually inspected or algorithms may be used to inspect the pH values to check for uniqueness. Generally, it is expected that when reagents in the mixture have different pKa values but their acid and base forms show similar color transformations with pH (for example, colors of all reagents changing from yellow to blue/red as they go from acid to base), the reagent combination should provide a unique pH vs. ODR plot.

Figure 8:
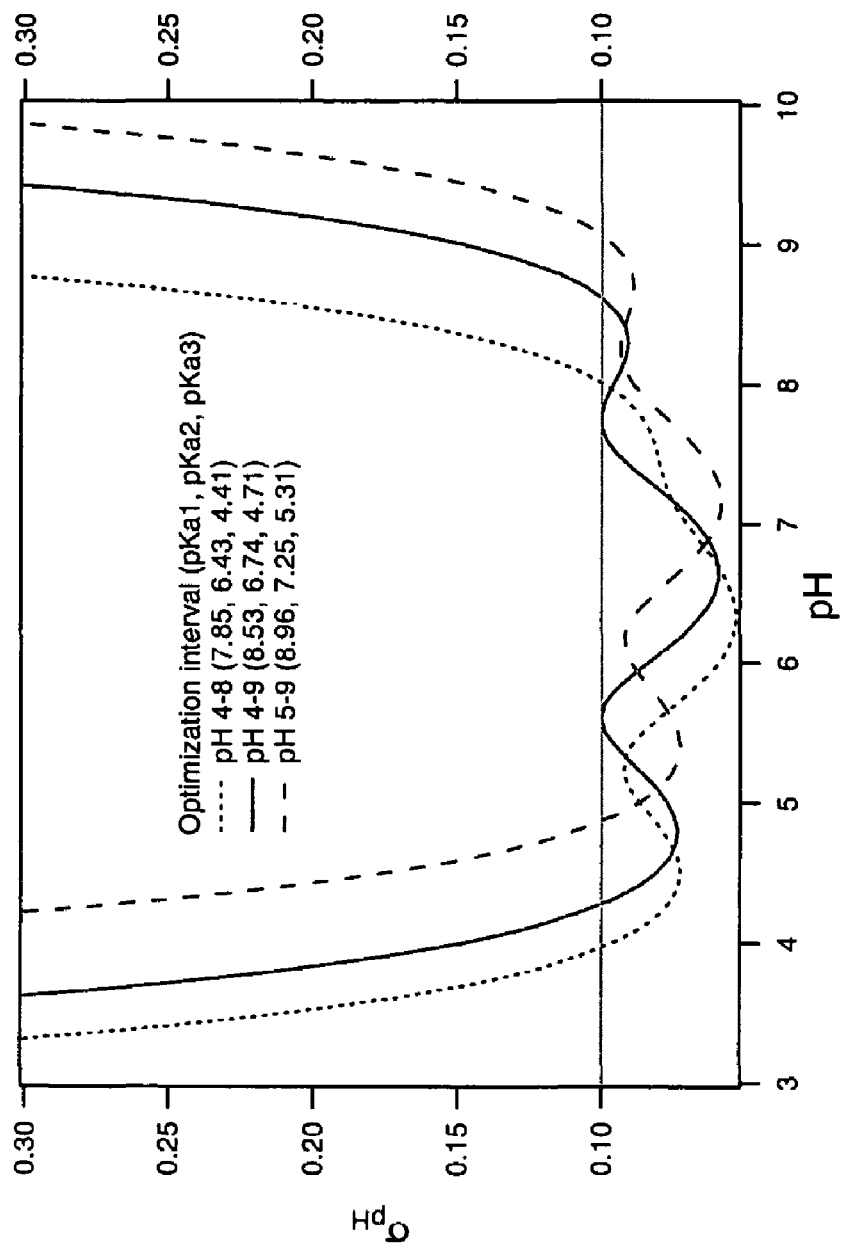
FIG. 8 is a plot showing the determination of the optimum pKa values for an equal weight mixture of three-reagents for various target pH intervals by optimizing objective function Equation (30) below.

It is also possible to optimize the reagent selection process (with a final check being done as discussed above for uniqueness). Thus, for a fixed mole fraction, pKa values of the reagents in the mixture may be optimized so as to maximize accuracy in the pH interval of interest. FIG. 8 lists optimum sets of pKa values of reagents in a three-reagent mixture for different pH intervals of interest. [For Equation (30), p is 0.5 and $w_i$ is 1.] For this example, the three-reagents had equal weight fractions, and epsilon values were fixed as provided in Table 1.

Reagents may also be chosen to allow pH measurement over discontinuous pH intervals of interest. Thus, in a two-reagent mixture of phenol red (pKa=7.79), for example, and bromophenol blue (pKa=4.11) where the pKa values are separated by more than 3 units, the pH intervals on the low end (2.8-5.1 units) and the high end (6.6-8.7) may be simultaneously targeted without any sensitivity for regions in between.

Figure 9A:
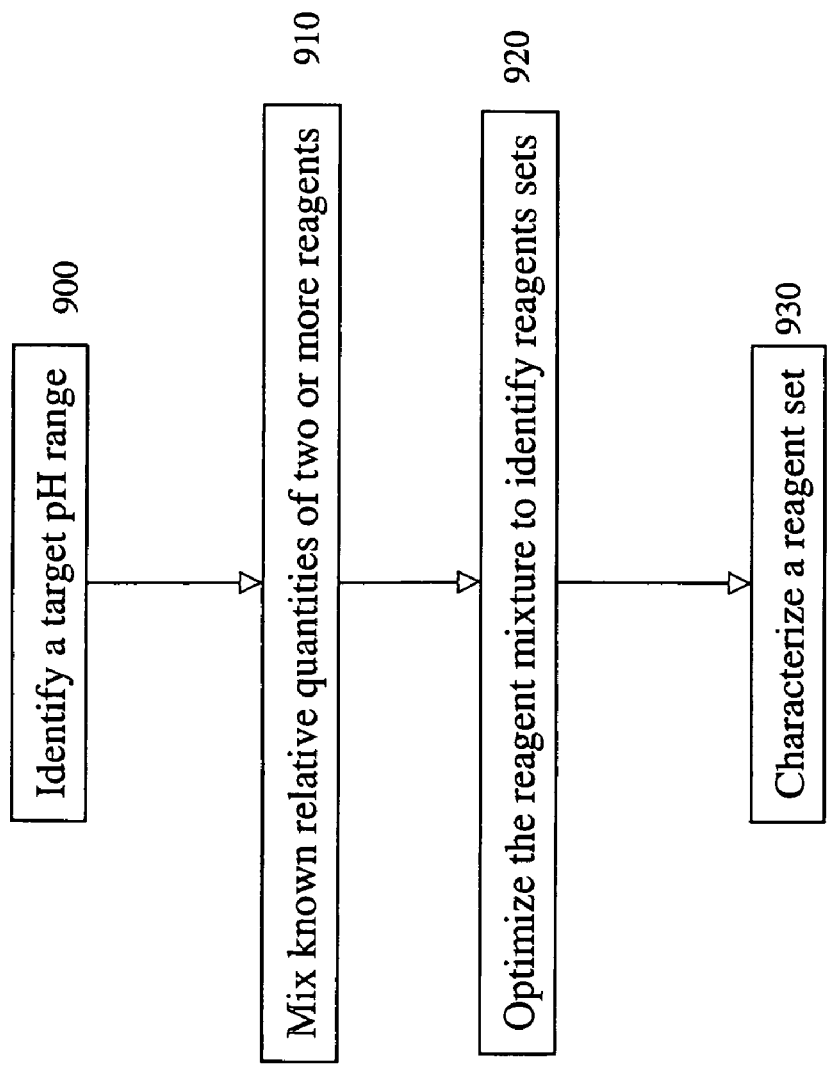
FIGS. 9(a) and (b) are schematics describing the overall optimization algorithm.
Figure 9B:
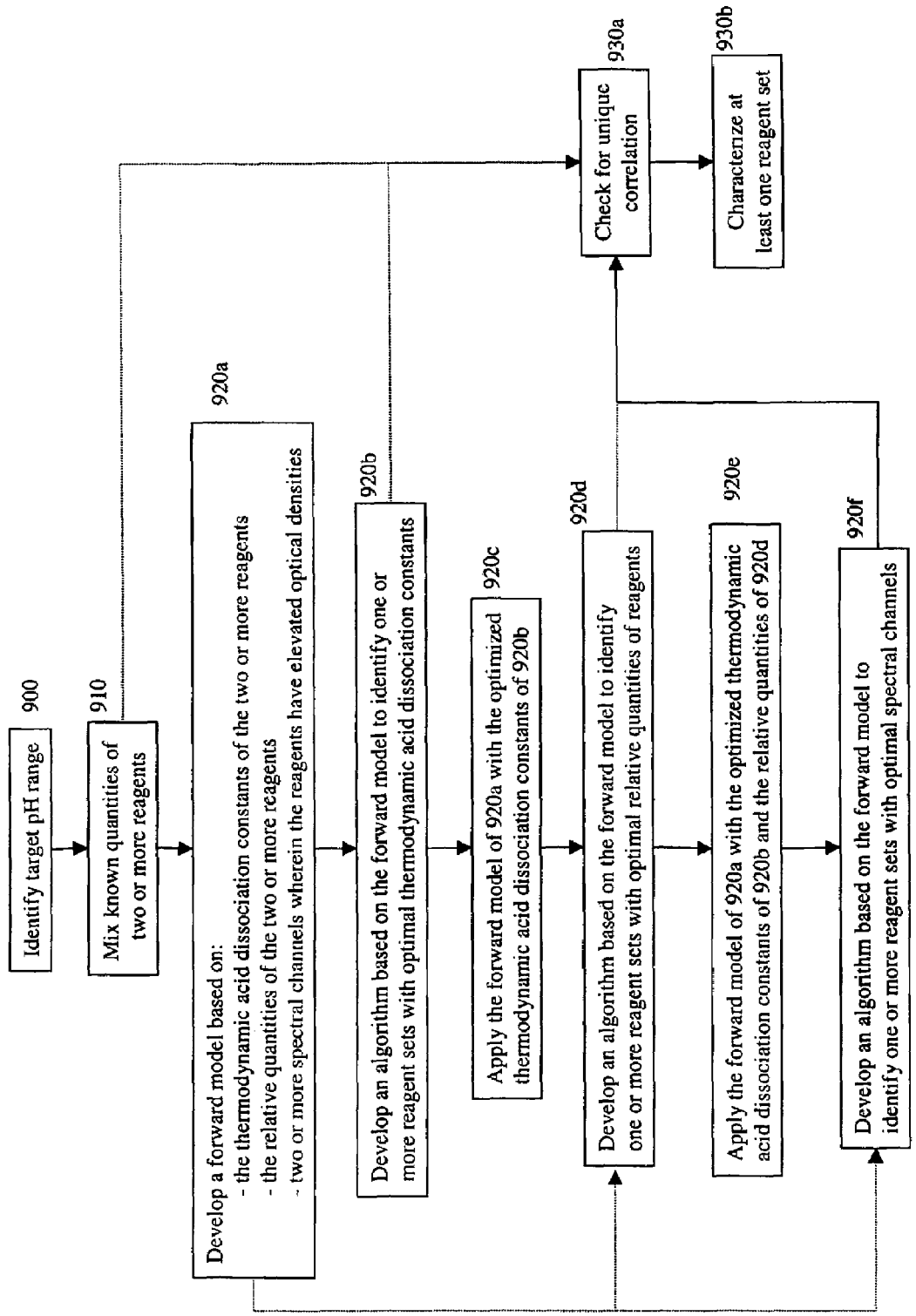

The general method of making and optimizing the pH indicator mixture is described in FIGS. 9(*a*) and (*b*). As shown in FIG. 9(*a*), first a target pH range is selected 900. Then, known relative quantities of the two or more reagents are mixed 910. The reagents are selected such that when mixed, the reagents cover a broader pH range or improved accuracy than if the reagents were used individually. It is noted that the present method does not require that absolute concentrations of the reagents be known; knowledge of relative (or fractional) quantities is sufficient. The reagent mixture is then optimized (for example, by trial and error, experimentation, or using forward modeling) to identify one or more sets of reagents that satisfy the target pH range 920. Once optimized reagent sets are identified, one or more of the reagent sets may be characterized to be used for spectroscopic pH measurement 930 (such as by developing functions of pH, OD, ODR, error deviations, etc.).

A non-limiting preferred algorithm is shown in FIG. 9(*b*). As in FIG. 9(*a*), a pH target range is identified 900 and known quantities of two or more reagents are mixed 910. Boxes 920*a*-920*f* describe a preferred method of optimizing the reagent mixtures. First, a forward model is developed 920*a* based on the three variables: (1) the thermodynamic acid dissociation constants which are dependent on the reagents selected; (2) the relative quantities of the reagents (it may be simplest to begin with equal quantities of reagents); and (3) the identification of two or more spectral channels wherein the reagents show elevated levels of optical densities. It may be preferred to identify common channels wherein all of the reagents show elevated levels of optical density. Next, an algorithm is developed 920*b* based on the forward model of 920*a* to identify sets of reagents having optimized thermodynamic acid dissociation constants. (It is noted that reagents having the exact thermodynamic acid dissociation constants as optimized may not be available. Accordingly, an "optimized" reagent set will include reagents have thermodynamic acid dissociation constants within acceptable range of the optimal value. Accordingly, numerous acceptable reagent sets may be identified.)

The procedure is then repeated for the optimized set of reagents 920*c*-920*d* using the optimized thermodynamic acid dissociation constants, relative weight fractions, and spectral channels. However, now the reagent sets are optimized to determine the optimal relative weight fractions for the reagent sets identified in 920*b*. The procedure is repeated once more for the optimized set of reagents 920*e*-920*f* using the optimized thermodynamic acid dissociation constants, the optimized relative weight fractions, and spectral channels. But, now the reagent sets are optimized to determine the optimal spectral channels for the reagent sets identified in 920*d*.

It is noted that each level of optimization need not be performed. One may chose to optimize for one or more (but not necessarily all) of: the thermodynamic equilibrium constants, relative quantities, or spectral channels at any time as shown by the dotted arrow to the left. At any point in the process, the optimized reagent sets may be checked for a unique correlation of pH as a function of ODR 930*a* and characterized for later use for spectroscopic pH measurement 930*b*. It is noted that the absolute concentration of the reagent mixture may also be adjusted to improve error (i.e., the signal to noise ratio.)

Apparatus Example

The present invention may be implemented in a laboratory or in various downhole fluid analysis tools. For example, the apparatus described in commonly owned co-pending U.S. patent application Ser. No. 10/667,639 filed Sep. 22, 2003, entitled "Determining Fluid Chemistry of Formation Fluid by Downhole Reagent Injection Spectral Analysis" (incorporated by reference herein in its entirety) is a preferred implementation of the present reagent mixture.

Figure 10:
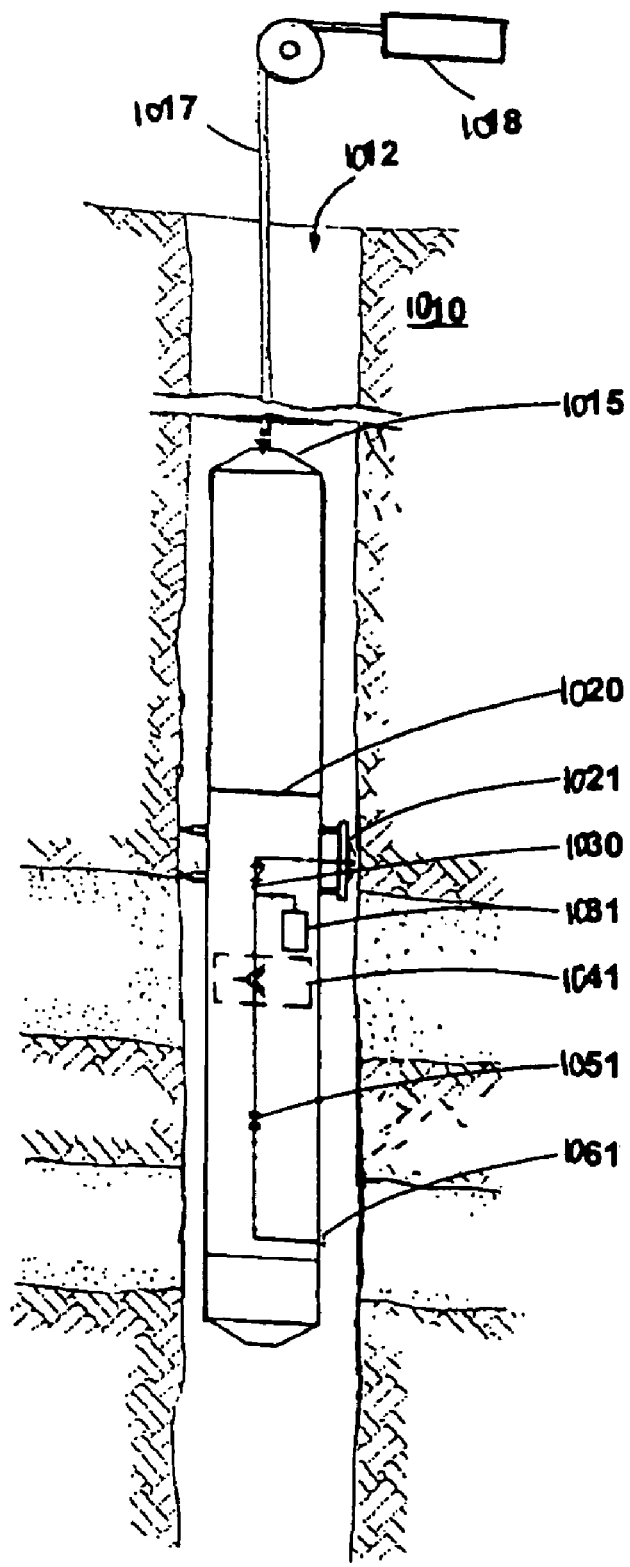
FIG. 10 is a schematic showing one application of the present invention.

One non-limiting embodiment of the present invention, as shown in FIG. 10, is a wireline formation tester 1015, including fluids analyzer 1020. The formation tester is shown downhole within borehole 1012 of formation 1010 suspended by logging cable 1017. Logging cable 1017 also couples the formation tester to surface system 1018. Fluids analyzer 1020 is located within formation tester 1015. Means for extracting fluid from the formation, in this case a probe 1021, is shown extending from the formation tester 1015. Major elements of fluids analyzer 1020 are fluid flow-line 1030, reagent container 1031, and spectral analyzer 1041. This embodiment further uses a flow-line pump (dual chamber piston pump) 1051 and main pump-out line 1061. It is noted that this figure is intended to depict a non-limiting embodiment useful for deploying the present invention. Other suitable elements may be included as dependent upon the specific application. For example, other configurations may be used to extract fluids from the formation, such as in a producing well or a monitoring well where a pump is used to obtain fluid samples. Accordingly, while FIG. 10 depicts a wireline application, the present invention may be deployed in other scenarios, such as permanent installations or a drilling environment.

While the invention has been described herein with reference to certain examples and embodiments, it will be evident that various modifications and changes may be made to the embodiments described above without departing from the scope and spirit of the invention as set forth in the claims.

What is claimed is:

1. A method of identifying one or more sets of reagents wherein the one or more sets of reagents is used for determining the pH of a sample, the method comprising:
   a. identifying a target pH measurement range of the sample and a target pH accuracy;
   b. identifying a plurality of reagents based on known reagent thermodynamic acid dissociation constants and spectral characteristics such that their combination is expected to satisfy the targeted pH range of the sample;
   c. identifying one or more spectral channels to make the pH measurement wherein the reagents have elevated optical densities;
   d. mixing known relative concentrations of two or more reagents of the plurality of reagents to create one or more sets of reagents;
   e. characterizing at least one reagent set of the one or more sets of reagents wherein characterizing includes developing a relationship between optical density ratio and pH based on the thermodynamic acid dissociation constants of the reagents, relative concentrations of the reagents, and one or more spectral channels;
   f. identifying the spectroscopic noise of a spectral analyzer to be used for the pH measurement;
   g. performing an error analysis for at least one reagent set of the one or more sets of reagents wherein the error analysis comprises developing a relationship between standard deviation in pH and spectroscopic noise in optical density based on the relation developed in step (e);
   h. optimizing the one or more sets of reagents with an optimization algorithm based on the developed relationship in step (g) to satisfy the target pH accuracy over the target pH measurement range of the sample and determine one of optimum values for relative concentrations or spectral channels or both; and
   i. characterizing the one or more optimized reagent set.

2. The method of claim 1, further comprising the step of characterizing the at least one of the one or more sets of optimized reagents by developing a relationship between optical density ratio and pH using the optimized parameters.

3. The method of claim 2, further comprising checking for uniqueness of the correlation between optical density ratio and pH.

4. The method of claim 2, wherein the one or more optimized sets of reagents is suitable for use in a downhole environment, the method further comprising:
   a. storing the optimized set of reagents in a reagent container coupled to a fluids analyzer, wherein said reagent mixture is capable of detecting a pH range broader than each reagent individually;
   b. positioning the fluids analyzer downhole;
   c. drawing formation fluid into the fluids analyzer;
   d. mixing formation fluid with the reagent mixture; and
   e. analyzing the optical density of said mixture of formation fluid and reagent mixture in one or more spectral channels to determine the pH of the formation fluid.

5. The method of claim 4, wherein said pH is determined to an accuracy of 0.5 pH units or less.

6. The method of claim 4, wherein analyzing the optical density is performed using two or more channels.

7. The method of claim 6, further comprising analyzing the optical density ratio.

8. The method of claim 4, comprising obtaining optical measurements in three or more channels and performing a regression analysis using said optical measurements.

9. The method of claim 1, further comprising optimizing absolute concentration of the one or more sets of reagents.

10. The method of claim 1, wherein the reagents show similar direction of spectral shift with changes in pH.

11. The method of claim 1, wherein identifying the spectroscopic noise includes one of signal to noise ratio of spectral signal or standard deviation and the optical density.

* * * * *